(12) United States Patent
Remias et al.

(10) Patent No.: US 9,409,125 B2
(45) Date of Patent: Aug. 9, 2016

(54) METHOD OF INCREASING MASS TRANSFER RATE OF ACID GAS SCRUBBING SOLVENTS

(71) Applicant: The University of Kentucky Research Foundation, Lexington, KY (US)

(72) Inventors: Joseph E. Remias, Lexington, KY (US); Cameron A. Lippert, Lexington, KY (US); Kunlei Liu, Lexington, KY (US)

(73) Assignee: THE UNIVERSITY OF KENTUCKY RESEARCH FOUNDATION, Lexington, KY (US)

( * ) Notice: Subject to any disclaimer, the term of this patent is extended or adjusted under 35 U.S.C. 154(b) by 488 days.

(21) Appl. No.: 13/853,292

(22) Filed: Mar. 29, 2013

(65) Prior Publication Data

US 2014/0294705 A1 Oct. 2, 2014

(51) Int. Cl.
| | |
|---|---|
| *B01D 53/14* | (2006.01) |
| *B01D 53/86* | (2006.01) |
| *C07F 9/54* | (2006.01) |
| *C07F 15/06* | (2006.01) |
| *C07F 3/00* | (2006.01) |

(52) U.S. Cl.
CPC ........ *B01D 53/8681* (2013.01); *B01D 53/1475* (2013.01); *B01D 53/1493* (2013.01); *C07F 3/003* (2013.01); *C07F 9/5456* (2013.01); *C07F 9/5463* (2013.01); *C07F 15/065* (2013.01); *B01D 2252/20431* (2013.01); *B01D 2252/20442* (2013.01); *B01D 2252/20447* (2013.01); *B01D 2252/20452* (2013.01); *B01D 2252/20484* (2013.01); *B01D 2252/20489* (2013.01); *B01D 2252/602* (2013.01); *B01D 2256/245* (2013.01); *B01D 2257/504* (2013.01); *Y02C 10/06* (2013.01); *Y02P 20/152* (2015.11)

(58) Field of Classification Search
None
See application file for complete search history.

(56) References Cited

U.S. PATENT DOCUMENTS

| | | |
|---|---|---|
| 4,240,922 A | 12/1980 | Sartori et al. |
| 4,376,101 A | 3/1983 | Sartori et al. |
| 4,407,784 A | 10/1983 | Blanc et al. |
| 4,545,965 A | 10/1985 | Gazzi et al. |
| 4,729,883 A | 3/1988 | Lam et al. |
| 5,026,904 A | 6/1991 | Lodge et al. |
| 5,618,506 A | 4/1997 | Suzuki et al. |
| 5,911,964 A | 6/1999 | Iwanami et al. |
| 6,165,432 A | 12/2000 | Rooney |
| 6,337,059 B1 | 1/2002 | Schubert et al. |
| 6,582,498 B1 | 6/2003 | Sass et al. |
| 6,921,733 B2 | 7/2005 | Mahajan |

(Continued)

FOREIGN PATENT DOCUMENTS

| | | |
|---|---|---|
| CA | 1277985 C | 12/1990 |
| JP | 11079725 A | 3/1999 |

(Continued)

OTHER PUBLICATIONS

Salanti et al., "Oxidation of Isoeugenol by Salen Complexes with Bulky Substituents", Int. J. Mol. Sci. 2010, 11, 912-926.*

(Continued)

*Primary Examiner* — Jonathan Johnson
*Assistant Examiner* — Anita Nassiri Motlagh
(74) *Attorney, Agent, or Firm* — King & Schickli, PLLC (57) ABSTRACT

A method of increasing the overall mass transfer rate of acid gas scrubbing solids is disclosed. Various catalyst compounds for that purpose are also disclosed.

6 Claims, 6 Drawing Sheets

(56) References Cited

U.S. PATENT DOCUMENTS

| | | |
|---|---|---|
| 7,056,482 B2 | 6/2006 | Hakka et al. |
| 7,601,315 B2 | 10/2009 | Ouimet |
| 7,758,673 B2 | 7/2010 | Brok et al. |
| 7,763,562 B2 | 7/2010 | Voskoboynikov et al. |
| 7,939,461 B2 | 5/2011 | Fukuzumi et al. |
| 8,329,929 B2 | 12/2012 | Matsunaga et al. |
| 2002/0081256 A1 | 6/2002 | Chakravarti et al. |
| 2008/0025893 A1 | 1/2008 | Asprion et al. |
| 2009/0214408 A1 | 8/2009 | Blake et al. |
| 2010/0105909 A1 | 4/2010 | Matsunaga et al. |
| 2010/0192770 A1 | 8/2010 | Andarcia et al. |
| 2010/0217029 A1* | 8/2010 | Sundermeyer et al. ......... 560/24 |
| 2011/0015059 A1 | 1/2011 | Matsunaga et al. |
| 2011/0168019 A1 | 7/2011 | Northrop et al. |
| 2011/0176981 A1 | 7/2011 | Jacquin et al. |
| 2012/0021897 A1 | 1/2012 | Iwata et al. |
| 2012/0063978 A1 | 3/2012 | Baugh et al. |
| 2012/0063980 A1 | 3/2012 | Kortunov et al. |
| 2012/0237421 A1 | 9/2012 | Millner et al. |

FOREIGN PATENT DOCUMENTS

| | | |
|---|---|---|
| JP | 2003260364 A | 9/2003 |
| WO | 2012034027 A1 | 3/2012 |

OTHER PUBLICATIONS

Sonar et al., "Synthesis and application of Co(salen) complexes containing proximal imidazolium ionic liquid cores", Can. J. Chem. 90: 60-70 (2012).*

J. Cullinane, et al.; "Kinetics of Carbon Dioxide Absorption into Aqueous Potassium Carbonate and Piperazine"; Industrial & Engineering Chemistry Research 2006, vol. 45, No. 8, pp. 2531-2545.

* cited by examiner

METHOD OF INCREASING MASS TRANSFER RATE OF ACID GAS SCRUBBING SOLVENTS

TECHNICAL FIELD

The present invention relates generally to various methods of increasing the overall mass transfer rate of acid gas scrubbing solvents utilizing various catalysts compounds.

BACKGROUND

The cleanup of acid gasses or sour gas, such as $CO_2$ in particular, from natural gas and in oil refining has been an extensively practiced technology. The industrial removal of $CO_2$ from natural gas dates back to the 1930's. In the $21^{st}$ century, due to the potential impact of anthropogenic $CO_2$ emissions on the climate, post-combustion $CO_2$ capture has gained tremendous attention. While several technologies exist for the removal of acid gasses one of the most commonly employed practices is the use of aqueous amines. Of these amines, tertiary amines are often used for natural gas applications due to their low energy of regeneration. For post-combustion $CO_2$ capture applications primary and secondary amines tend to be in part favored by their faster rate at the low $CO_2$ driving force condition. Regardless of the application, the mass transfer rate in the absorber column dictates the size of the column (capital cost) used and, consequently, has a substantial impact on the overall process cost. An overall process depicting a thermal swing process is presented in FIG. 1. An aqueous amine solution is circulated between the absorber 10 and stripper 12. The gas, containing $CO_2$, enters the bottom of the absorber where it contacts the aqueous amine absorbent removing it from the gas stream. The liquid solution, $CO_2$ rich amine solution, is then passed through a heat exchanger 14 to improve efficiency before being heated to a higher temperature in the stripper 12. The stripper 12 removes the $CO_2$ as a gas from the amine solution to produce a lean, or $CO_2$ deficient solution. The lean solution is returned to the absorber 10 by way of the heat exchanger 14 to repeat the process.

In order to minimize system capital (absorber cost) it is important to maximize the overall mass transfer rate for the scrubber system as there is a direct correlation between the two. This invention relates to methods for this purpose as well as to catalyst compounds useful in those methods.

SUMMARY

A method is provided for increasing the overall mass transfer rate of acid gas scrubbing solvents. The method comprises adding a catalyst compound to a fluid stream including an acid gas and an acid gas scrubbing solvent wherein that catalyst compound has a chemical formula:

where:
(a) M is any group VII B through XII B element;
(b) E is any combination of N, O, S having a net $2^-$ charge per individual ligand;
(c) $R_{1,2,4}$=—H, —COOH, —[OCH$_2$CH$_2$]$_n$—OR$_9$, CH$_3$, amine, amide, phosphate, —OH, —R$_5$OH, —[SO$_3$]$^-$;
(d) $R_3$=—H, —COOH, —[OCH$_2$CH$_2$]$_n$—OR$_9$, amine, amide, phosphate, —OH, —R$_5$OH, —[SO$_3$]$^-$, —[(CH$_2$)$_n$Q]$^+$ [A]$^-$;
(e) $R_5$=C$_1$-C$_5$ alkyl; (f) A=monovalent anion: Cl, Br, I, F, PF$_6$, BF$_4$, acetate, trifluoroacetate, ClO$_4$, NO$_3$;
(g) Q=monovalent cation: PX$_3$ where X=alkyl, cyclic alkyl, aryl, O-alkyl, O-aryl, N(R$_6$)$_3$ where R$_6$=alkyl, cyclic alkyl, N-heterocyclic ring, imidazole;

(h)

where Y=—H, —COOH, —R$_7$OOH (R$_7$=alkyl ranging from 2-10 carbons);
—[OCH$_2$CH$_2$]$_n$—OR$_9$; —OH; —SO$_3$; —NO$_2$; amine, amide; or where $Z_{1-6}$=—H, any alkyl, —COOH, —R$_8$OOH (R$_8$=alkyl ranging from 2-10 carbons), —[OCH$_2$CH$_2$]$_n$—OR$_9$; OH; SO$_3$; NO$_2$; amine, amide; and
(i) where n=1 to 10; and
(j) R$_9$=H or alkyl.

In one possible embodiment the catalyst compound has a chemical formula:

where R=any alkyl
M=Co, Zn.

In another possible embodiment the catalyst compound has a chemical formula:

where M=Co, Zn.

In another possible embodiment the catalyst compound has a chemical formula:

where M=Co, Zn
R=any alkyl.

In still another possible embodiment the catalyst compound has a chemical formula:

where M=Co, Zn.

In yet another possible embodiment the catalyst compound has a chemical formula:

where M=Co, Zn.

In yet another possible embodiment the catalyst compound has a chemical formula:

where M=Co, Zn.

In still another possible embodiment the catalyst compound has a chemical formula:

where M=Co, Zn.

In any of the embodiments the acid gas scrubbing solvent includes an amine or a mixture of amines. In one possible embodiment the acid gas scrubbing solvent includes a mixture of (a) a promoter amine and (b) a tertiary amine.

In one possible embodiment the acid gas scrubbing solvent includes chemical compounds selected from a group including but not limited to, monoethanolamine (MEA), 1-amino-2-propanol (1A2P), 3-amino-1-propanol, 2-amino-1-propanol, 2-amino-1-butanol, 1-amino-2-butanol, 3-amino-2-butanol, 2-(methylamino)ethanonol (MAE), 2-(ethylamino) ethanol, morpholine, piperazine (PZ), 1-methylpiperazine (NMP), 2-methylpiperazine, hydroxypiperadine, 2-piperidineethanol, N-aminoethylpierazine (AEP), aminopropylmorpholine, 4-aminopiperidine, 2-amino-2-methyl-1-propanol (AMP), diethanolamine (DEA), diisopropanolamine (DIPA), glycine, alanine, β-alannine, sarcosine, ethylene diamine (EDA), 1,3-propanediamine, 1,4-butanediamine, 1,5-pentanediamine, 1,6-hexanediamine, methyldiethanolamine (MDEA), triethanolamine (TEA), dimethylethanolamine (DMEA), N,N,N',N'-tetramethyl-1,8-naphthalenediamine, diethylmonoethanolamine, dipropylmonoethanolamine, 1,4-dimethylpiperazine, N N,N',N'-tetramethyl-1,6-hexanediamine, N,N,N',N'-tetrakis (2-hydroxyethyl)ethylenediamine, N,N,N',N',N''-pentamethyldiethylenetriamine, N,N,N',N'-tetramethylethylenediamine, N,N,N',N'-tetramethylpropane-1,3-diamine, N,N,N',N'-tetramethylbutane-1,4-diamine, N,N,N',N'-tetramethyl-1,5-pentanediamine, alkali carbonate, and mixtures thereof.

Further the catalyst compound is provided at a concentration of between about 0.05 mM and about 100 mM.

Various catalyst compounds are also claimed.

BRIEF DESCRIPTION OF THE DRAWING FIGURES

The accompanying drawings incorporated herein and forming a part of the specification, illustrate several aspects of the present method and together with the description serve to explain certain principles thereof. In the drawings.

DETAILED DESCRIPTION

This document relates generally to methods of increasing overall mass transfer rate of acid gas scrubbing solvents as well as to novel transition metal monomer complexes incorporating a single transition metal atom.

The method may be broadly described as comprising adding a catalyst compound to a fluid stream including an acid gas and an acid gas scrubbing solvent. The catalyst compound has a chemical formula:

where:

(a) M is any group VII B through XII B element;

(b) E is any combination of N, O, S having a net 2⁻ charge per individual ligand;

(c) $R_{1,2,4}$=—H, —COOH, —[OCH$_2$CH$_2$]$_n$—OR$_9$, amine, amide, phosphate, —OH, —R$_5$OH, —[SO$_3$]⁻;

(d) $R_3$=—H, —COOH, —[OCH$_2$CH$_2$]$_n$—OR$_9$, amine, amide, phosphate, —OH, —R$_5$OH, —[SO$_3$]⁻, —[(CH$_2$)$_n$Q]⁺ [A]⁻;

(e) $R_5$=$C_1$-$C_5$ alkyl;

(f) A=monovalent anion: Cl, Br, I, F, PF$_6$, BF$_4$, acetate, trifluoroacetate, ClO$_4$, NO$_3$;

(g) Q=monovalent cation: PX$_3$ where X=alkyl, cyclic alkyl, aryl, O-alkyl, O-aryl, N(R$_6$)$_3$ where R$_6$=alkyl, cyclic alkyl, N-heterocyclic ring, imidazole;

(h)

where Y=—H, —COOH, —R$_7$OOH (R$_7$=alkyl ranging from 2-10 carbons);

—[OCH$_2$CH$_2$]$_n$—OR$_9$; —OH; —SO$_3$; —NO$_2$; amine, amide; or n = 1-3 where $Z_{1-6}$=—H, any alkyl, —COOH, —$R_8$OOH ($R_8$=alkyl ranging from 2-10 carbons), —[OCH$_2$CH$_2$]$_n$—OR$_9$; OH; SO$_3$; NO$_2$; amine, amide;
(i) where n=1 to 10; and
(j) $R_9$=H or alkyl.

In one particular embodiment the catalyst compound has a chemical formula:

where R=any alkyl
M=Co, Zn.

In another particular embodiment the catalyst compound has a chemical formula:

where M=Co, Zn.

In another possible embodiment the catalyst compound has a chemical formula:

where M=Co, Zn
R=any alkyl.

In another possible embodiment the catalyst compound has a chemical formula:

where M=Co, Zn.

In yet another possible embodiment the catalyst compound has a chemical formula:

where M=Co, Zn.

In yet another possible embodiment the catalyst compound has a chemical formula:

where M=Co, Zn.

In still another possible embodiment the catalyst compound has a chemical formula:

where M=Co, Zn.

For any embodiment of catalyst compound, the terms "alkyl" or "any alkyl", when not otherwise stipulated, include at least $C_2$-$C_{10}$ alkyl compounds.

For any of the method embodiments the acid gas scrubbing solvent may include an amine. In one possible embodiment the acid gas scrubbing solvent includes a mixture of (a) a promoter amine, selected from a group of primary and secondary amines and (b) a tertiary amine.

Such a mixture is described in detail in copending U.S. patent application Ser. No. 13/853,186, filed on Mar. 29, 2013 and entitled "Solvent and Method for Removal of an Acid Gas from a Fluid Stream", the full disclosure of which is incor porated herein by reference. Promoter amines useful in the present method include, but are not limited to, the primary and secondary amines such as 3-N-sulfonylamine (SA), 3-aminopropionitrile (APN), diethyl 2-aminoethanephosphonate (EtP2), N-methyltetrahydrothiophen-3-amine 1,1-dioxide, 2,2'-sulfonyldiethanamine, 3,3'-sulfonyldipropaneamine, 4,4'-sulfonyldibutanenamine, 2-aminoethyl methyl sulfone, 4-aminobutanenitrile, 6-aminohexanenitrile, 3-(methylamino)propanenitrile, diethyl[2-(methylamino)ethyl] phosphonate, diethyl(3-aminopropyl)phosphonate, diethyl (4-aminobutyl)phosphonate, diethyl(5-aminopentyl) phosphonate, diethyl(6-aminohexyl)phosphonate, 2-(tert-butoxy)ethan-1-amine, N-methyl-2-[(2-methyl-2-propanyl) oxy]ethanamine and mixtures thereof.

Tertiary amines and carbonate based salts useful in the present method include but are not limited to methyldiethanolamine (MDEA), triethanolamine (TEA), N,N,-dialkylethanolamine, N,N,N',N'-tetraalky-1,8-naphthalenediamine, N,N,-dialkylbenzylamine, 1,4-dialkylpiperazine, N,N,N',N'-tetraalkyl-1,6-hexanediamine, N,N,N',N'-tetraalkyl-1,5-pentanediamine, N,N,N',N'-tetraalkyl-1,4-butanediamine, N,N,N',N'-tetraalkyl-1,3-propanediamine, N,N,N',N'-tetraalkyl-1,2-ethanediamine, N,N,N',N'-tetrakis(2-hydroxyethyl) ethylenediamine, N,N,N',N',N''-pentaalkyldiethylenetriamine, N,N,N',N',N''-pentaalkyldipropylaminetriamine, N,N,-dialkylcyclohexylamine, N,N,N',N'-tetraalkylbis (aminoethyl)ether, N,N,-dimethyl-2(2-aminoethoxy) ethanol, alkali carbonates where alkyl represents any methyl, ethyl, propyl, butyl isomer, and mixtures thereof. In one possible embodiment, the catalyst compound is provided in the fluid stream with a concentration of between about 0.05 mM and about 50 mM. In another possible embodiment the catalyst compound is provided in the fluid stream with a concentration of between 50.1 mM and 75 mM. In yet another possible embodiment the catalyst compound is provided in the fluid stream with a concentration of between about 75.1 mM and 100 mM.

Primary and secondary amines useful in the present method include but are not limited to monoethanolamine (MEA), 1-amino-2-propanol (1A2P), 3-amino-1-propanol, 2-amino-1-propanol, 2-amino-1-butanol, 3-amino-2-butanol, 1-amino-2-butanol, 2-(alkylamino)ethanonol (MAE), diglycolamine, morpholine, piperazine (PZ), 1-methylpiperazine (NMP), 2-methylpiperazine, hydroxypiperadine, hydroxymethylpiperazine, 2-piperidineethanol, N-aminoethylpierazine (AEP), aminopropylmorpholine, 4-aminopiperidine, 3-aminopiperidine, 2-amino-piperidine, diethanolamine, 2-amino-2-methyl-1-propanol (AMP), diethanolamine (DEA), diisopropanolamine (DIPA), glycine, alanine, β-alannine, sarcosine, isopropanolamine, benzylamine, ethylene diamine (EDA), 1,3-propanediamine, 1,4-butanediamine, 1,5-pentanediamine, 1,6-hexanediamine.

Figure 1:
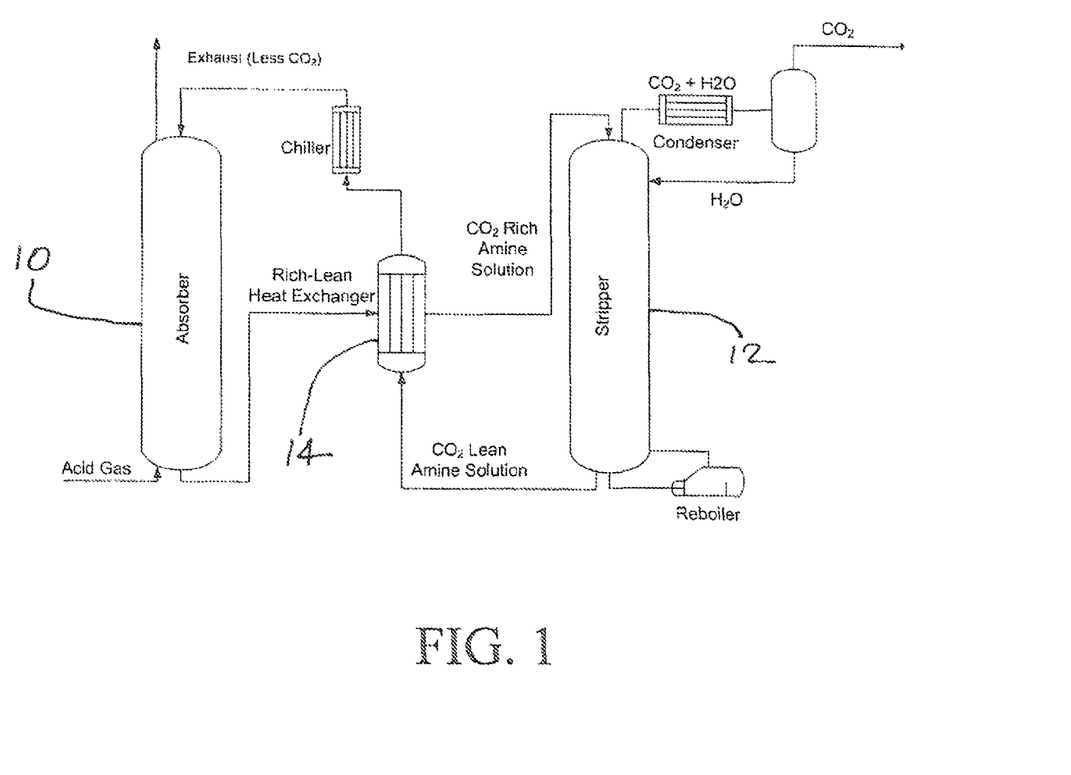
FIG. 1 is a schematical illustration of a process for removing acid gas from a fluid stream utilizing solvent and thermal swing regeneration.

In any of the embodiments, the catalyst compound must be stable under the relatively high temperature conditions (e.g. between perhaps 70 and 170° C.) found within the stripper 12. The present catalyst compounds meet this requirement.

The following examples further illustrate how to synthesize or manufacture certain representative catalysts used in the method of increasing the overall mass transfer rate of acid gas scrubbing solvents.

Example 1

CAER-C1P

Preparation of $H_2LP$

To a solution of 1-(3-formyl-4-hydroxybenzyl)triphenylphosphonium chloride (5.00 g, 11.55 mmol) in dry ethanol (40 mL) was added ethylenediamine (0.40 mL, 6 mmol) slowly at room temperature. The resulting solution was stirred at reflux temperature for 3 h. The solution was allowed to cool to room temperature and the solvent was removed under reduced pressure. The yellow residue was dissolved in dichloromethane (50 mL) and slowly added dropwise to 150 mL of stirring ethyl acetate to give a bright yellow powder which was collected via filtration (4.9958 g, 97%) in >95% purity based on $^1$H NMR spectroscopy.

Preparation of CAER-C1P

A 100-mL round-bottom flask was charged with $H_2LP$ (4.594 g, 5.17 mmol) and $CoCl_2.(H_2O)_6$ (1.3541 g, 5.7 mmol), and EtOH (40 mL) was added to make a slurry. 2 equiv. of $Et_3N$ (1.5 mL, 11 mmol) was added and the mixture was heated at reflux for 3 hours. The mixture was cooled to room temperature and the solvent was removed under reduced pressure to give a brown powder. The brown powder was washed with ice cold water to remove ammonium salts and then triturated with ether to give the desired product as a brown solid (3.2295 g, 63%)

Example 2

CAER-C3I

Preparation of H₂LI

To a solution of 1-(3-formyl-4-hydroxybenzyl)-3-methylimidazolium hexafluorophosphate (5.00 g, 13.80 mmol) in dry ethanol (40 mL) was added ethylenediamine (0.50 mL, 7.5 mmol) slowly at room temperature. The resulting solution was stirred at reflux temperature for 6 h. The solution was allowed to cool to room temperature after which a solid separated out. The solid was washed with ethanol (3×5 mL) then ether (3×10 mL) and dried in vacuo to give a yellow solid (5.4375 g, 97%) in >95% purity based on $^1$H NMR spectroscopy.

Preparation of CAER-C3I

A 100-mL round-bottom flask was charged with H₂LI (5.011 g, 6.68 mmol) and ZnCl₂ (1.3630 g, 10 mmol), and EtOH (40 mL) was added to make a slurry. 2 equiv. of Et₃N (2.0 mL, 14 mmol) was added and the mixture was heated at reflux for 3 hours. The mixture was cooled to room temperature and a pale yellow solid was collected via filtration (4.6390 g, 85%) in >95% purity based on $^1$H NMR spectroscopy.

Example 3

CAER-C3P*

Preparation of H₂LP*

A 100-mL round-bottom flask was charged with 5-chloromethyl-2-hydroxybenzaldehyde (10.3327 g, 60.4 mmol) and dissolved in ethyl acetate (40 mL) and triethylphosphite (11.5 mL, 67 mmol) was added. The mixture was heated at reflux (80° C.) for 3 hours. The mixture was cooled to room temperature and the solvent removed under reduced pressure to give triethoxy(3-formyl-4-hydroxybenzyl)phosphonium chloride as a viscous oil which was used without further purification. The viscous oil (10.003 g, 30 mmol) was dissolved in ethanol (40 mL) and ethylenediamine (1.2 mL, 18 mmol) was added slowly. The mixture was heated at reflux (80° C.) for 3 hours. The mixture was cooled to room temperature and the solvent was removed under reduced pressure to give a thick, yellow, oily substance. The oil was washed with ether (3×10 mL). The ether was evaporated slowly over 24 hours to produce a thick, yellow, viscous oil (10.2215 g, 98%) in ~85% purity based on $^1$H NMR spectroscopy.

Preparation of CAER-C3P*

A 100-mL round-bottom flask was charged with H₂LP* (5.028 g, 7.2 mmol) and ZnCl₂ (1.4652 g, 10.8 mmol), and dissolved in EtOH (40 mL). 2 equiv. of Et₃N (2.1 mL, 15 mmol) was added and the mixture was heated at reflux for 3 hours. The mixture was cooled to room temperature and the solvent was removed under reduced pressure to give a thick, oily substance. The oil was washed with ether (3×10 mL) to produce a white solid which was removed via filtration. The ether was evaporated slowly over 24 hours to produce a thick, colorless, viscous oil (4.8832 g, 89%) in >90% purity based on $^1$H NMR spectroscopy.

Example 4

CAER-C4

Preparation of H₂L4

A 50 mL round bottom flask was charged with 2 equiv. 4-formyl-3-hydroxybenzoic acid (0.2471 g, 1.49 mmol) and dissolved in EtOH followed by addition of 1 equiv. ethylenediamine (50 µL, 0.75 mmol). The mixture was heated at reflux for 2 hr. The reaction mixture was cooled to room temp. and a yellow powder was collected via filtration (247.3 mg, 93%) >95% purity based on $^1$H NMR spectroscopy.

Preparation of CAER-C4

A 100-mL round-bottom flask was charged with H₂L4 (0.06980 g, 0.196 mmol) and ZnCl₂ (0.0433 g, 0.318 mmol), and EtOH was added to make a slurry. 2 equiv. of Et₃N (58 µL, 0.417 mmol) was added and the mixture was heated at reflux for 3 hours. The mixture was cooled to room temperature and a pale yellow solid was collected via filtration (66.7, 81%) in >95% purity based on $^1$H NMR spectroscopy.

Example 5

CAER-C5$_z$

Preparation of H₂L5

A 100-mL round bottom flask was charged with 3,4-diaminobenzoic acid (2.0067 g, 13.2 mmol) and dissolved in EtOH. 2 equiv. salicylaldehyde (2.8 mL, 26.3 mmol) was added and the reaction mixture was heated at reflux for 2 hr, at which point an orange solid had formed. The mixture was cooled to room temp, and the orange solid was collected via filtration (1.8274, 38%). The orange filtrate was stored at 8° C. for 15 hours and a second crop of orange solids was collected via filtration (2.3211 g, 48%), for a combined 86% yield in >95% purity based on $^1$H NMR spectroscopy.

Preparation of CAER-C5$_Z$

A 100-mL round-bottom flask was charged with H$_2$L5 (0.4921 g, 1.37 mmol) and ZnCl$_2$ (0.3224 g, 2.37 mmol), and EtOH was added to make a slurry. 2 equiv. of Et$_3$N (390 µL, 2.8 mmol) was added and the mixture was heated at reflux for 3 hours. The mixture was cooled to room temperature and a pale yellow/orange solid was collected via filtration (0.5613, 97%) in >95% purity based on $^1$H NMR spectroscopy.

Example 6

CAER-CII

Preparation of CAER-CII

A 100-mL round-bottom flask was charged with H$_2$LI (3.023 g, 4.04 mmol) and CoCl$_2$.(H$_2$O)$_6$ (1.0641 g, 4.44 mmol), and EtOH (40 mL) was added to make a slurry. 2 equiv. of Et$_3$N (1.2 mL, 8.63 mmol) was added and the mixture was heated at reflux for 3 hours. The mixture was cooled to room temperature and a dark brown solid was collected via filtration (3.592 g, 93%).

Example 7

CAER-C3P

Preparation of CAER-C3P

A 100-mL round-bottom flask was charged with H$_2$LP (5.002 g, 5.63 mmol) and ZnCl$_2$ (1.3630 g, 10 mmol), and EtOH (40 mL) was added to make a slurry. 2 equiv. of Et$_3$N (1.75 mL, 12 mmol) was added and the mixture was heated at reflux for 3 hours. The mixture was cooled to room temperature and a pale yellow solid was collected via filtration (4.9790 g, 93%) in >95% purity based on $^1$H NMR spectroscopy.

Catalyst Testing in Concentrated Primary Amines: Breakthrough Method

Figure 2:
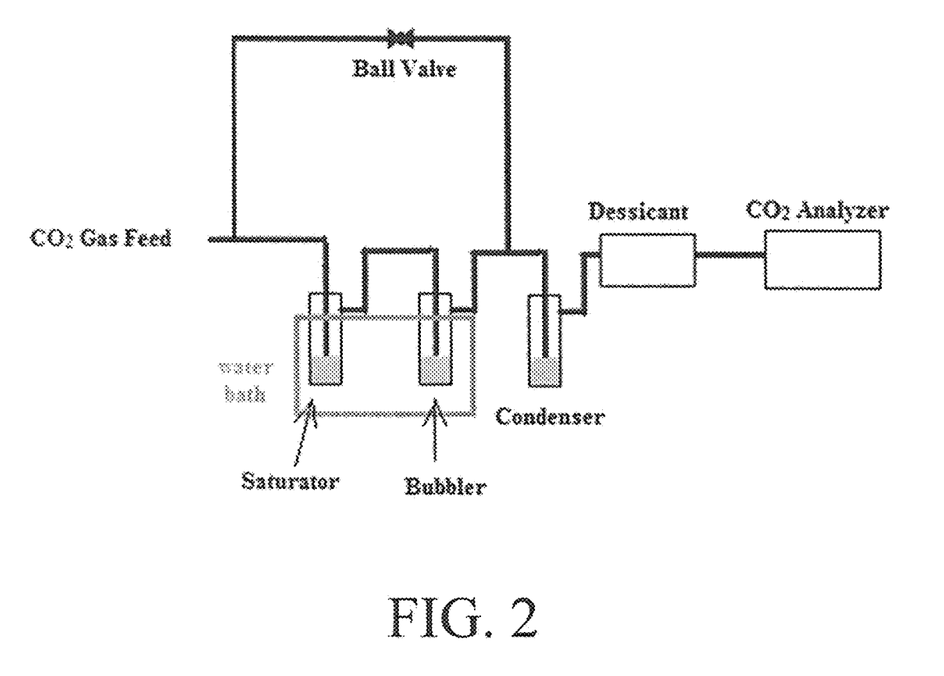
FIG. 2 is a schematical illustration of a simple $CO_2$ bubbling apparatus used for catalyst testing.

A schematic of the apparatus used is shown in FIG. 2. Briefly, 0.85 L/min feed gas containing ~13% CO$_2$ mixed with N$_2$ is firstly saturated with water in the first impinger and then bubbled through 15 ml of testing solvent in the second impinger. Both the saturator and bubbler are immersed in a water bath at 40° C. The gas effluent is dried through an ice condenser and a Drierite tube before it is analyzed for CO$_2$ concentration using a dual-beam NDIR online CO$_2$ analyzer (Model 510, HORIBA, Ltd). Data of CO$_2$ outlet concentration with respect to time is continuously recorded through a LABVIEW® package with 1 second interval. A line that bypasses the saturator and the bubbler is set up for inlet CO$_2$ concentration determination. Before each experiment, the alkalinity of the testing solvent is precisely determined through acid-base titration.

The difference of inlet and outlet CO$_2$ concentration represents the absorbed amount of CO$_2$ at a particular time. The integration of the concentration difference represents the CO$_2$ loading as expressed $$\text{CO}_2 \text{ Loading } (t)(\text{mol CO}_2/\text{kg solution}) = \frac{\int_0^t (C_{in} - C_{out}(t))dt}{m_{sol}} \quad \text{Eq 1}$$

in which $C_{in}$ is the CO$_2$ feed gas rate in mol/s, $C_{out}$ is the CO$_2$ effluent rate in mol/s, t is the time in second, and $m_{sol}$ is the mass of solution in kg. The CO$_2$ loading at $C_{out}=C_{in}$ is the equilibrium CO$_2$ capacity at 13% CO$_2$ and 40° C. With the alkalinity (mol N/kg of solution) of the solution known, the CO$_2$ loading can also be written as $$\alpha = \frac{\text{CO2 Loading (mol CO}_2/\text{kg solution)}}{\text{Alkalinity (mol N/kg solution)}} = \frac{\text{mole of CO}_2}{\text{mole of N}} \quad \text{Eq 2}$$

In addition, the absorption rate can be described by the derivate of CO$_2$ loading with respect to time:

$$\text{Absorpton rate (mol CO}_2/\text{kg solution/s)} = \frac{d\text{CO}_2 \text{ Loading}}{dt} \quad \text{Eq 3}$$

Figure 3:
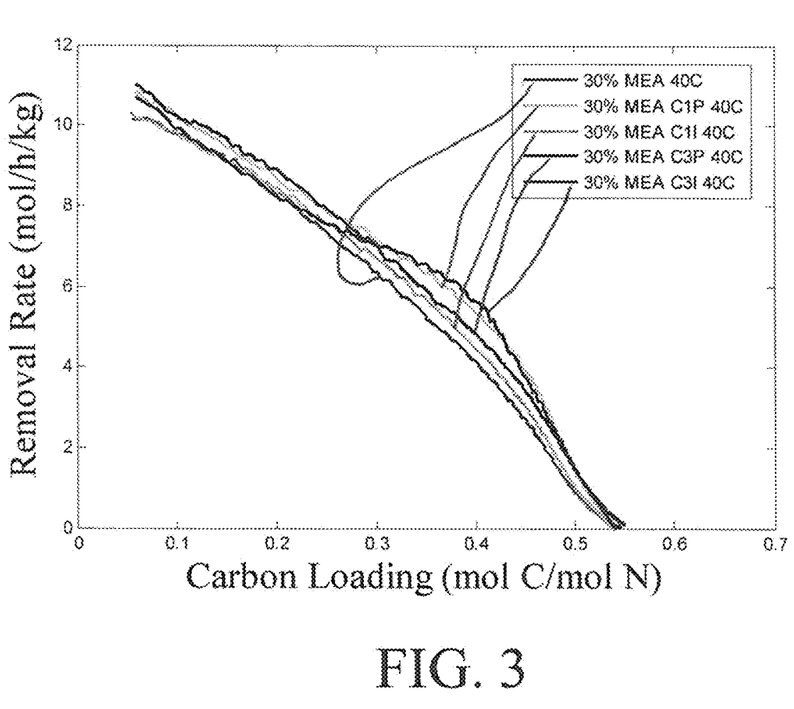
FIG. 3 is a graphical illustration of removal rate versus carbon loading for various catalysts used with 30 wt % MEA at 40° C.
Figure 4:
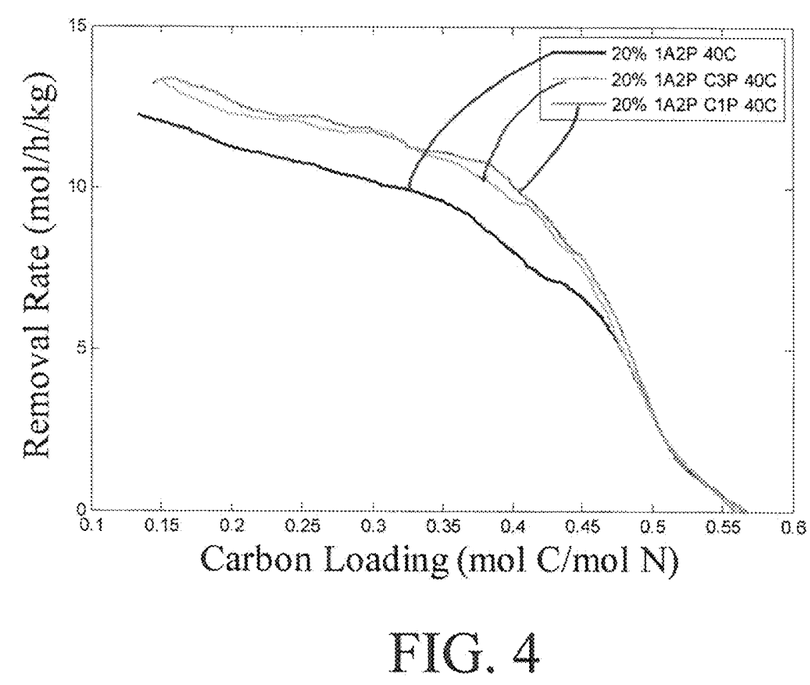
FIG. 4 is a graphical illustration of removal rate versus carbon loading for various catalysts in 20% 1-amino-2-propanol solvent with 13% $CO_2$ at 40° C.

As illustrated in FIGS. 3 and 4, the current catalyst compounds improve the removal rate of a 30 wt % MEA acid gas scrubbing solvent.

Catalyst Testing in Concentrated Primary Amines: WWC Method

Figure 5:
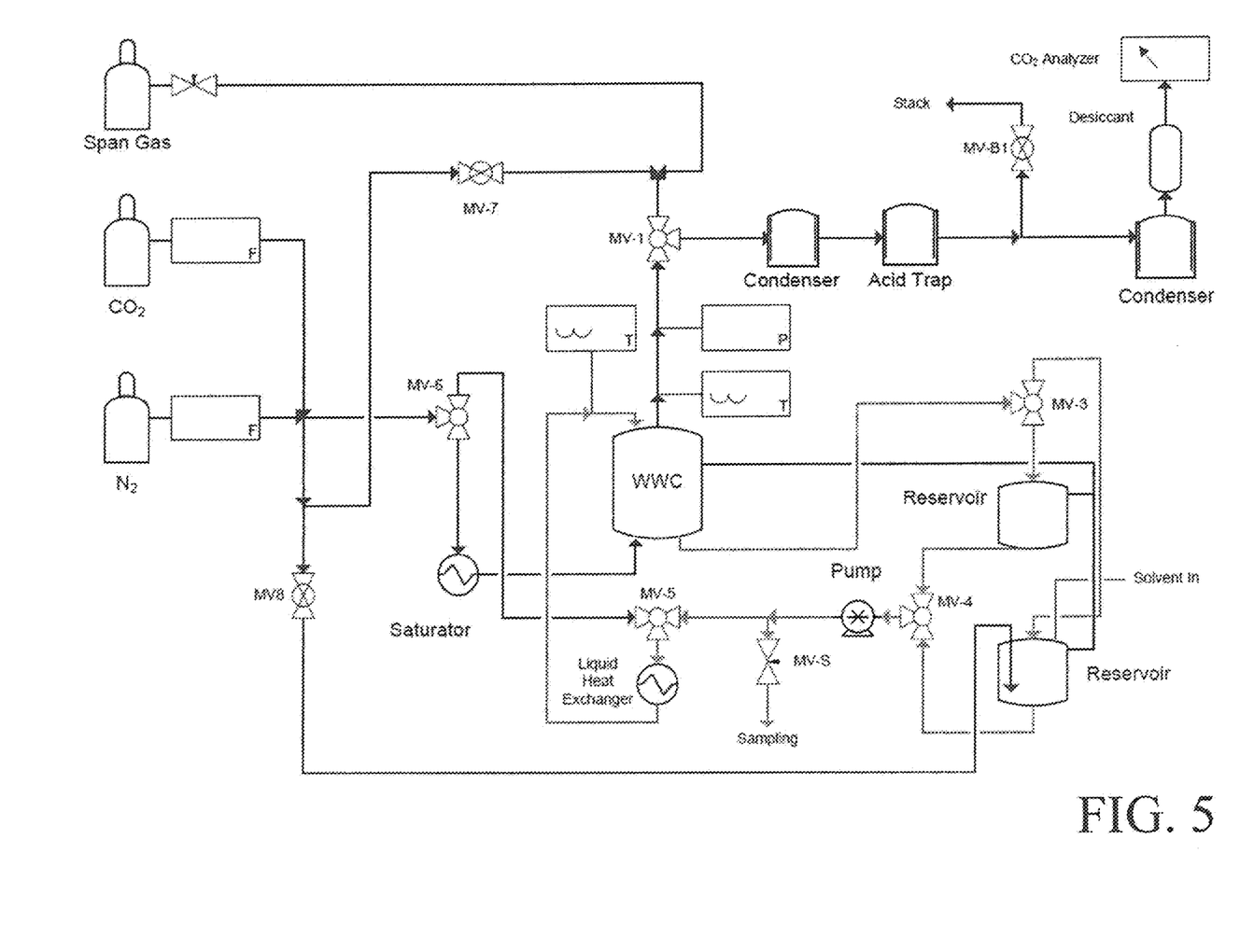
FIG. 5 is a schematical illustration of a wetted wall column (WWC) apparatus used in testing the catalysts.
Figure 6:
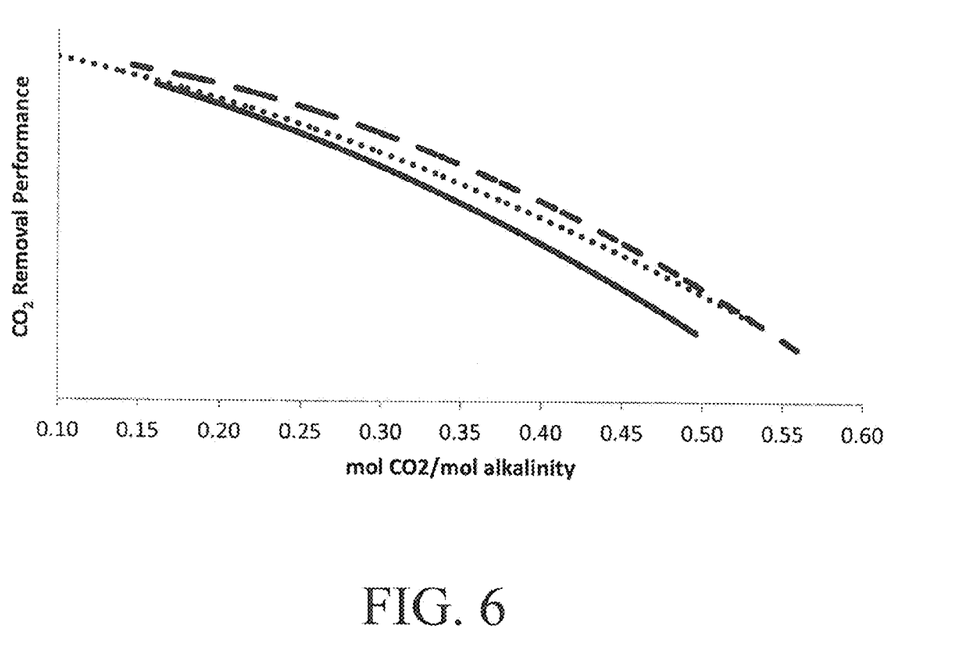
FIG. 6 is a graphical comparison of $CO_2$ overall mass transfer as measured on a wetted wall column for 30 wt % MEA at 40° C. with catalyst CAER-C1P and CAER-C3I.

The wetted wall column (WWC) is used to determine mass transfer of CO$_2$ into a process absorption solvent. The WWC apparatus is illustrated in FIG. 5. The improved overall mass transfer resulting from the use of two catalysts is illustrated in FIG. 6.

In each test, solvent is loaded to a molCO$_2$/molN level of approximately 0.1 with CO$_2$ by sparging the solution reservoir with a concentrated CO$_2$/N$_2$ mixture. The initially loaded solution is then circulating through the wetted wall column and a pre-heater which heats the solution to the desired temperature. Once the solution is thermally stable, a simulated flue gas stream (CO$_2$ balanced with N$_2$) saturated with water flows into the wetted wall column. In the wetted wall column, liquid flows downwards on the outside surface on an annular tube while CO$_2$ gas stream flows upwards around the annular tube. CO$_2$ absorption from the gas phase into the liquid takes place along the tube's wall. Gas effluent from the WWC is dried and analyzed by an infrared $CO_2$ analyzer for $CO_2$ concentration determination. $CO_2$ inlet concentration is analyzed by directing the gas to bypass the WWC. A liquid sample downstream of the WWC is collected at each solution carbon loading and tested for total liquid $CO_2$ loading, viscosity, density, and pH measurements. Liquid film thickness is calculated by Eq. 1. The bulk solution is then loaded with more $CO_2$ and the data collection cycle is repeated $$\delta = \sqrt[3]{\frac{3\mu Q_{sol}}{\rho g W}} \quad \text{Eq. 1}$$

in which $\mu$ is the viscosity, $Q_{sol}$ is the liquid flow rate, p is the density of liquid, and W is the circumference of the column.

The overall mass transfer coefficient at the operating condition can be calculated from Eq. 2.

$$K_G = \frac{N_{CO_2}}{\Delta P_{CO_2}} \quad \text{Eq. 2}$$

in which $N_{CO_2}$ is the flux of $CO_2$, $K_G$ is the overall mass transfer coefficient, $\Delta P_{CO_2}$ is the log mean of driving force which is defined by

$$\Delta P_{CO_2} = \frac{P_{CO_2}^{in} - P_{CO_2}^{out}}{\ln\left(\frac{P_{CO_2}^{in} - P_{CO_2}^*}{P_{CO_2}^{out} - P_{CO_2}^*}\right)} \quad \text{Eq. 3}$$

in which $P_{CO_2}^{in}$ and $P_{CO_2}^{out}$ represent the $CO_2$ partial pressure at the inlet and outlet of the wetted wall column, and $P^*_{CO_2}$ is the equilibrium partial pressure of $CO_2$. The $P^*_{CO_2}$ is obtained by making the flux $N_{CO_2}$ to be zero at zero driving force and solving the 2 equations simultaneously using a trial-and-error routine in MATLAB®.

The foregoing has been presented for purposes of illustration and description. It is not intended to be exhaustive or to limit the embodiments to the precise form disclosed. Obvious modifications and variations are possible in light of the above teachings. All such modifications and variations are within the scope of the appended claims when interpreted in accordance with the breadth to which they are fairly, legally and equitably entitled.

What is claimed:

1. A catalyst compound having a chemical formula:

where M=Co, Zn
R=any alkyl.

2. A method of increasing overall mass transfer rate of acid gas scrubbing solvents, comprising:
adding the catalyst compound of claim 1 to a fluid stream including an acid gas and an acid gas scrubbing solvent.

3. The method of claim 1 wherein said acid gas scrubbing solvent includes an amine.

4. The method of claim 1, wherein said acid gas scrubbing solvent includes a mixture of a primary or secondary amine and a tertiary amine.

5. The method of claim 1, wherein said acid gas scrubbing solvent includes a material selected from a group consisting of monoethanolamine (MEA), 1-amino-2-propanol (1A2P), 3-amino-1-propanol, 2-amino-1-propanol, 2-amino-1-butanol, 1-amino-2-butanol, 3-amino-2-butanol, 2-(alkylamino)ethanonol (MAE), diglycolamine, morpholine, piperazine (PZ), 1-methylpiperazine (NMP), 2-methylpiperazine, hydroxypiperadine, hydroxyalkylpiperazine, 2-piperidineethanol, N-aminoethylpierazine (AEP), aminopropylmorpholine, 4-aminopiperidine, 3-aminopiperidine, 2-amino-piperidine, diethanolamine, 2-amino-2-methyl-1-propanol (AMP), diethanolamine (DEA), diisopropanolamine (DIPA), glycine, alanine, β-alannine, sarcosine, isopropanolamine, benzylamine, methyldiethanolamine (MDEA), triethanolamine (TEA), alkali carbonate, N,N,-dialkylethanolamine, N,N,N',N'-tetraalky-1,8-naphthalenediamine, N,N,-dialkylbenzylamine, 1,4-dialkylpiperazine, N,N,N',N'-tetraalkyl-1,6-hexanediamine, N,N,N',N'-tetraalkyl-1,5-pentanediamine, N,N,N',N'-tetraalkyl-1,4-butanediamine, N,N,N',N'-tetraalkyl-1,3-propanediamine, N,N,N',N'-tetraalkyl-1,2-ethanediamine, N,N,N',N'-tetrakis (2-hydroxyethyl)ethylenediamine, N,N,N',N'''-pentaalkyldiethylenetria mine, N,N,N',N'''-pentaalkyldipropylaminetriamine, N,N,-dialkylcyclohexylamine, N,N,N',N'-tetraalkylbis(aminoethyl)ether, N,N,-dimethyl-2(2-aminoethoxy)ethanol, where alkyl represents any methyl, ethyl, propyl, butyl isomer, and mixtures thereof.

6. The method of claim 1, wherein said catalyst compound is provided at a concentration of between about 0.05 mM and about 100 mM.

* * * * *